United States Patent
Nam

(10) Patent No.: US 9,603,684 B2
(45) Date of Patent: Mar. 28, 2017

(54) APPARATUS FOR MANUFACTURING TOOTH MODEL AIDS

(71) Applicant: MUNGYO GYPSUM & ENGINEERING CORPORATION, Gimhae-si Gyeongsangnam-do (KR)

(72) Inventor: Doo Suek Nam, Busan (KR)

(73) Assignee: MUNGYO GYPSUM & ENGINEERING CORPORATION (KR)

( * ) Notice: Subject to any disclaimer, the term of this patent is extended or adjusted under 35 U.S.C. 154(b) by 0 days.

(21) Appl. No.: 14/427,608

(22) PCT Filed: Jan. 19, 2015

(86) PCT No.: PCT/KR2015/000511
§ 371 (c)(1),
(2) Date: Mar. 11, 2015

(87) PCT Pub. No.: WO2015/111882
PCT Pub. Date: Jul. 30, 2015

(65) Prior Publication Data
US 2016/0317259 A1    Nov. 3, 2016

(30) Foreign Application Priority Data
Jan. 21, 2014    (KR) ........................ 10-2014-0007000

(51) Int. Cl.
A61C 13/08    (2006.01)
A61C 13/00    (2006.01)
A61C 13/34    (2006.01)

(52) U.S. Cl.
CPC ........ *A61C 13/0028* (2013.01); *A61C 13/081* (2013.01); *A61C 13/34* (2013.01)

(58) Field of Classification Search
CPC .... A61C 13/0028; A61C 13/081; A61C 13/34
See application file for complete search history.

(56) References Cited

U.S. PATENT DOCUMENTS 5,968,171 A * 10/1999 Sunaga .............. B60H 1/00964
713/1

FOREIGN PATENT DOCUMENTS

JP    2008-167810    *    7/2008
KR    10-2006-0070052        7/2006
(Continued)

OTHER PUBLICATIONS

Electronic translation of KR 101258150 published Apr. 2013.*

*Primary Examiner* — Jill Heitbrink
(74) *Attorney, Agent, or Firm* — Innovation Counsel LLP

(57) ABSTRACT

Disclosed is an apparatus for manufacturing a tooth model aids. The apparatus for manufacturing a tooth model, which is configured to dewax when molding a tooth model so as to manufacture a dental denture, may include an outer housing, an inner container installed in an inside of the outer housing, a flask unit installed in an inner space part of the inner container. The flask unit includes a mounting plate on which a flask is configured to be mounted, and a cover, the mounting plate of the flask unit includes a wax collection hole on a bottom of the mounting plate, and the cover includes a nozzle which is configured to selectively inject hot water or steam to the flask, the nozzle being formed at a location corresponding to a location of the flask.

13 Claims, 3 Drawing Sheets

(56) References Cited

FOREIGN PATENT DOCUMENTS

| KR | 10-2010-0091412 | | 9/2010 |
|----|----|----|----|
| KR | 101258150 | * | 4/2013 |
| KR | 10-2013-0065611 | | 6/2013 |

* cited by examiner

APPARATUS FOR MANUFACTURING TOOTH MODEL AIDS

CROSS-REFERENCE TO RELATED APPLICATIONS

This application claims priority to and the benefit of Korean Patent Application No. 10-2014-0007000, filed on Jan. 21, 2014 and PCT Application No PCT/KR2015/000511, filed on Jan. 19, 2015 the entire contents of which are incorporated herein by reference.

BACKGROUND

1. Technical Field

The present inventive concept relates to an apparatus for manufacturing a tooth model aids, and in particular to an apparatus for manufacturing a tooth model aids which makes it possible to easily and fully remove wax from a denture when forming a tooth model for manufacturing a dental denture.

2. Background Art

In general, a tooth model is used as a clinical material for the sake of a correction of teeth and a manufacture of a new denture in a dental clinic.

In addition, a conventional method for manufacturing a synthetic resin denture may consist of a denture plate model burying process, a dewaxing process, a drying and releasing agent coating process, a synthetic resin injection process, a polymerization process, etc.

The conventional method for manufacturing a denture will be described. In the denture plate model burying process, a denture plate model made from a ceramic material or a plastic material is arranged inside of a flask and is fixed using a fixing gypsum at a plastic bottom plate.

At this time, a solid state wax is planted inside of the flask. The solid state wax serves to fix the denture plate model. The solid state wax is removed during a dewaxing process. During the dewaxing process, the solid state wax is heated to a high temperature and is melted and is removed.

When the tooth model is mixed with water, it turns into pasty water with a high viscosity. The impression material with wax component which is hardened as time passes by is used, and an impression material component, namely, a wax component is attached to the surface of the finished tooth model.

As a conventional method for removing wax, there is an apparatus for forming a dental denture (Korean Patent Publication Registration No. 10-0656467). The apparatus for forming a dental denture by injecting a resin melted in a melting furnace into a flask may include a clamp unit which is detachable from the melting furnace and serves to fix both side surfaces of the flask using the clamp or unclamp operations using air pressure, in which a cylindrical resin injection pipe is detachable from the melting furnace, and a cylindrical resin injection pipe detachable from the melting furnace, with resin being filled inside of the resin injection pipe; a pressurizing unit which is configured to descend and arranged at the top of the clamp unit and serves to inject the resin stored in the resin injection pipe with a predetermined pressure into the interior of the flask; an air pressure adjusting unit which is connected to the pressurizing unit and serves to supply air to the pressurizing unit and to adjust the pressure; and a control unit which is electrically connected to the clamp unit and the air pressure adjusting unit and serves to control the ascending and descending speeds of the pressurizing unit and the air pressure of the air pressure adjusting unit. The air pressure adjusting unit and the clamp unit may be driven by the air supplied through the upper and lower air supply pipes, so the apparatus may be widely used irrespective of the kinds of resins, thus forming various kinds of dentures fast and efficiently.

According to the conventional apparatus for manufacturing a tooth model aids granted to the applicant of the present inventive concept (Korean Patent Publication Registration No. 10-1023612), there is provided a method for dewaxing economically and efficiently in a method for manufacturing a synthetic resin denture, which method is characterized in that a wax may be removed economically and easily when removing wax from a denture inside of a flask by pressurizing at a high temperature so as to provide an apparatus for manufacturing a synthetic resin denture plate. An additional cost is not necessary for the sake of cleaning work of wax after a pressurizing and dewaxing process. Since the wax itself may be removed, the removed wax may be recycled while preventing any environment contamination. When such an apparatus for manufacturing a tooth model aids is implemented, it is possible to easily and fully remove wax from the denture by only using boiling water, and a large scale of facility is not necessary, which leads to the saving of cost, and when heating and pressurizing using a separate metallic dummy plate, the flask may be fixed safely.

However, in case where the tooth model aids is manufactured using the conventional apparatus, the wax may be mixed with other impurities while the wax is melted and flows downward to a recycling container, so the recycling of the wax is impossible, while causing environment contamination.

In addition, the procedure where the wax is removed by using boiling water is complicated, and it needs to consume lots of time and water, so the conventional apparatus is uneconomical.

SUMMARY

Accordingly, the present inventive concept is made in an effort to resolve the problems in the conventional art. It is an object of the present inventive concept to provide an apparatus for manufacturing a tooth model aids which makes it possible to easily remove solid wax which is used to fix and dewax a tooth model aids.

To achieve the above object, there is provided an apparatus for manufacturing a tooth model, which is configured to dewax when molding a tooth model so as to manufacture a dental denture, which may include an outer housing, an inner container installed in an inside of the outer housing, a flask unit installed in an inner space part of the inner container. The flask unit includes a mounting plate on which a flask is configured to be mounted, and a cover, the mounting plate of the flask unit includes a wax collection hole on a bottom of the mounting plate, and the cover includes a nozzle which is configured to selectively inject hot water or steam to the flask, the nozzle being formed at a location corresponding to a location of the flask.

The apparatus may further includes a water tank, a steam supply pipe connected between an upper portion of the water tank and the cover, and a hot water supply pipe connected between the lower portion of the water tank and the cover.

The apparatus may further include a water path supply pipe selectively connecting the cover to the steam supply pipe or the hot water supply pipe.

The flask may include a plurality of flasks and the water path supply pipe further comprising branches, each of the branches respectively connected to one of the plurality of flasks.

The flask may include a plurality of flasks and the water path supply pipe further comprising branches, each of the branches respectively connected to one of the plurality of flasks.

The inner container may include a drainage hole at a bottom of the inner container, the drainage being formed on the lowest portion of the bottom of the inner container.

The flask may include a guide hole, a resin injection port, an investment injection hole and a wax drainage port.

The apparatus for manufacturing a tooth model aids according to the present inventive concept makes it possible to very easily remove solid wax which is used to fix and dewax a tooth model aids, and time for extracting solid wax may be saved, so the present inventive concept is economical and has high efficiency.

BRIEF DESCRIPTION OF THE DRAWINGS

The present inventive concept will become better understood with reference to the accompanying drawings which are given only by way of illustration and thus are not limitative of the present inventive concept, wherein.

DETAILED DESCRIPTION

The present inventive concept is directed to an apparatus for manufacturing a tooth model aids.

An apparatus for manufacturing a tooth model, which is configured to dewax when molding a tooth model so as to manufacture a dental denture, may include an outer housing which includes a space part in its inside; and an outer cover which serves to block the outer housing from the outside, wherein at the upper side of the outer housing, an inner container is installed in the inside of the outer housing wherein the upper side of the inner container is open and includes a space part, and a flask unit is installed in the inner space part of the inner container, wherein a flask including a denture shape in the inside thereof is mounted on the flask unit, and the flask unit includes a mounting plate 141 on which the flask is mounted, and a cover configured to open or close the upper side of the flask. In addition, a pair of flask fixing keys configured to limit the flask and a wax collection hole are formed at the top of the mounting plate of the flask unit. A pair of support units are vertically fixed at one side. The cover is rotatably hinged at an end portion of the support unit. Beneath the cover, the nozzle is installed so as to supply water or steam to the portions corresponding to the resin injection port of the flask when the flask is mounted on the mounting plate.

The present inventive concept will be described in more detail with reference to the accompanying drawings.

Figure 1:
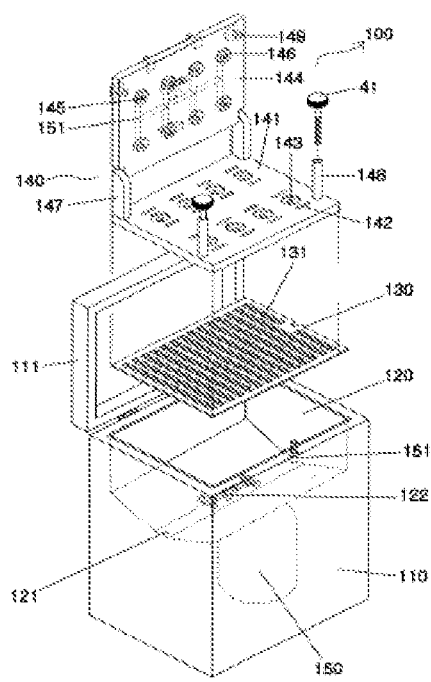
FIG. 1 is an exploded perspective view illustrating an apparatus for manufacturing a tooth model aids according to the present inventive concept.
Figure 2:
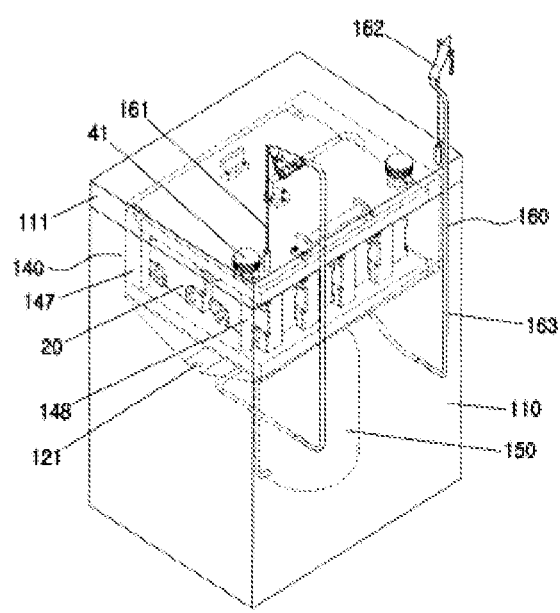
FIG. 2 is a perspective view illustrating an apparatus for manufacturing a tooth model aids according to the present inventive concept.
Figure 3:
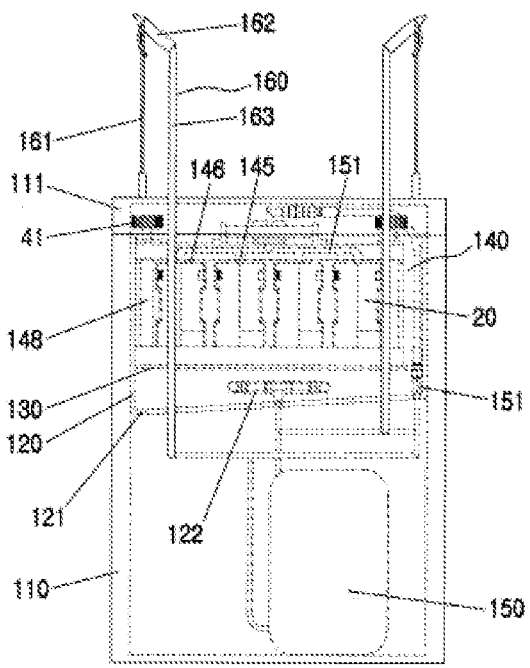
FIG. 3 is a cross sectional view illustrating an apparatus for manufacturing a tooth model aids according to the present inventive concept.
Figure 4:
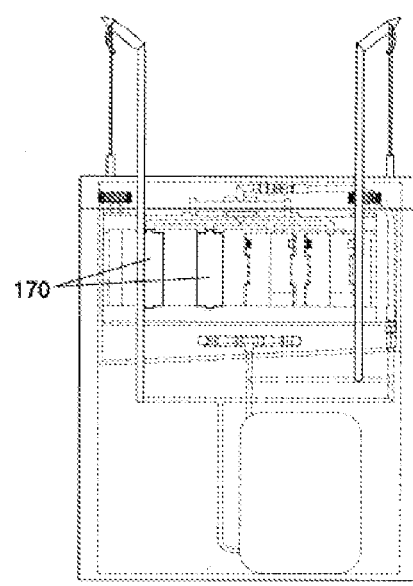
FIG. 4 is a cross sectional view illustrating a state where a guide rod is engaged instead of the flask in FIG. 3.
Figure 5:
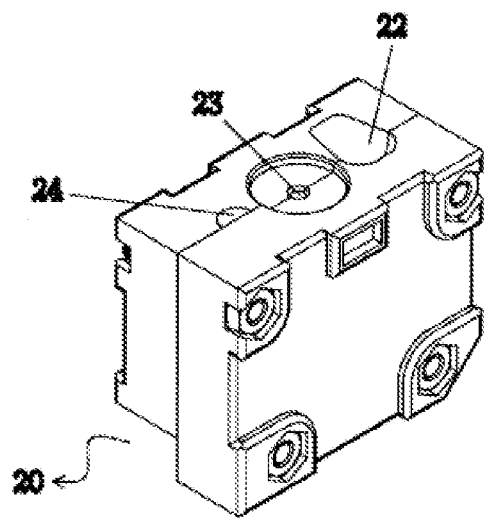
FIG. 5 is an enlarged perspective view illustrating a flask of an apparatus for manufacturing a tooth model aids according to the present inventive concept.
Figure 6:
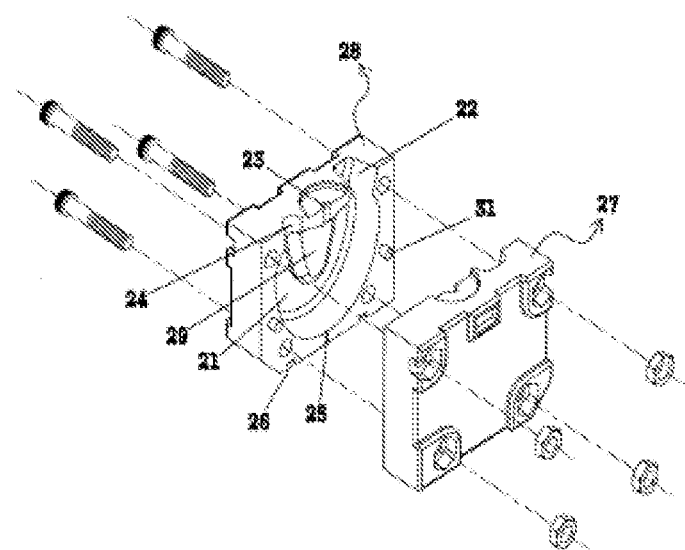
FIG. 6 is an exploded perspective view illustrating a flask of an apparatus for manufacturing a tooth model aids according to the present inventive concept.

FIG. 1 is an exploded perspective view illustrating an apparatus for manufacturing a tooth model aids according to the present inventive concept, FIG. 2 is a perspective view illustrating an apparatus for manufacturing a tooth model aids according to the present inventive concept, FIG. 3 is a cross sectional view illustrating an apparatus for manufacturing a tooth model aids according to the present inventive concept, FIG. 4 is a cross sectional view illustrating a state where a guide rod is engaged instead of the flask in FIG. 3, FIG. 5 is an enlarged perspective view illustrating a flask of an apparatus for manufacturing a tooth model aids according to the present inventive concept, and FIG. 6 is an exploded perspective view illustrating a flask of an apparatus for manufacturing a tooth model aids according to the present inventive concept.

The flask 20 may be described first before the apparatus for manufacturing the tooth model aids according to the present inventive concept is described.

The flask 20 is used to take a model of the denture of the tooth model aids based on the tooth shape of a user. The typical denture is made by taking a model of a user's tooth shape using an impression material and casting a denture based on the taken model.

When manufacturing the denture casting, the flask 20 is generally used. The flask 20 has an inner side and an outer side which are provided in a form of one pair and are engaged to match with each other. The flask 20 accommodates a molded gypsum of a tooth model aids casting.

A wax is provided between the molded gypsum inside of the flask and the denture plate model (tooth model), so the tooth model may be easily separated from the molded gypsum.

The apparatus for manufacturing the tooth model aids 100 according to the present inventive concept may include an outer housing 110 having a space part formed inside of the outer housing 110, and an outer cover 111 configured to block the outer housing 110 from the outside. In the outer housing 110, an inner container 120 is installed having an open top and a space part formed inside of the inner container 120. A support plate 130 configured to divide the inner space into an upper part and a lower part is inserted in the interior of the inner container 120. A flask unit 140 on which a flask 20 is mounted is installed at the top of the support plate 130.

As illustrated in FIG. 1, the outer housing 110 is configured with its top open, and includes a space part in the interior thereof, an outer cover 111 is hinged at one side of the top of the outer housing 110. Thus, the outer cover 111 may open and close easily.

In addition, an inner container 120 is provided inside of the outer housing 110, and the inner container 120 is installed at the top of the inside of the outer housing 110. Since the inner container 120 is installed at the top of the outer housing 110, a space part is formed below the inner container 120.

A water tank 150 is installed in the space part. The water is connected to an electric heater, etc. which is a hating means for heating water, thus supplying hot water or steam to the inner container 120 and the flask unit 140.

The water inside of the water tank 150 is heated by the electric heater. Hot liquid water is present at the lower side of the inside of the water tank 150, and water vapor (steam) is present at the upper side of the water tank 150.

Meanwhile, the inner container 120 installed at the top of the water tank 150 has an open top and a space part in the inside. A vertical cross section may be a shape of ⌒ having open top.

In addition, as illustrated in FIG. 3, the inner container 120 may include a bottom surface which is tilted to form a slanted surface, and a drainage hole 121 is formed at the lowest bottom surface, so the water in the inside of the inner container 120 may be easily drained to the outside.

In addition, a drainage pipe is engaged to the drainage hole 121, thus easily discharging impurities, water, etc. in the inside of the inner container to the outside.

The shape of the inner container may be altered as long as the impurities, water, etc. in the inside of the inner container can be easily discharged to the outside.

In addition, a steam supply nozzle 122 is installed at the bottom surface of the inner container. The steam supply nozzle 122 is connected to the top of the water tank 150, thus supplying steam into the inside of the inner container 120.

Meanwhile, as illustrated in FIGS. 1 and 3, the support plate 130 is mounted in the inside of the inner container 120. The support plate 130 serves to divide the inner space of the inner container 120 into an upper part and a lower part, and the bottom surface of the space of the upper side is made flat, so the flask unit 140 can be stably mounted.

In addition, the support plate 130 is formed in a shape of a quadrangular plate. A plurality of through holes 131 passing through the upper and lower directions are formed through the support plate 130.

Meanwhile, the flask unit 140 is mounted on the upper surface of the support plate 130. The flask 20 will be first described in detail with reference to FIGS. 5 and 6 before the flask unit 140 is described.

The flask 20 may be used to manufacture the denture aids and have a left side body 27 and a right side body 28. The resin injection port 23 into which resin is injected is formed at the upper engaging unit to which the left side body 27 and the right side body 28 are engaged. An investment injection port 22 into which an investment gypsum is injected is formed at a portion spaced apart by a regular interval from the resin injection port 23, and a space part 21 is formed in the inside of the left and right side bodies 27 and 28.

In addition, a denture plate model made of a wax material is inserted in the empty space, and the investment is injected through the investment injection port 22, and the denture made of the wax material and the investment are inserted in the hollow part 21 and are heated. A wax drainage port 25 through which the melted wax is discharged is formed at the bottom of the engaging parts of the left and right side bodies 27 and 28. Resin is injected through the resin injection port 23 and into the empty space formed after the denture plate model is melted.

The flask 20 may include a resin injection port 23 formed at the upper side of the flask 20 for receiving resin, an investment injection port 22 formed at the upper side of the flask 20 for receiving an investment, a guide hole 24 formed at the upper side of the flask 20 for confirming the injection amount of the investment injected through the investment injection port 22, and a wax drainage port 25 formed at the bottom of the flask 20 for discharging wax.

The flask 20 is formed in a shape of a quadrangular box and is provided in a form of a pair of its left and right sides, which are engaged with each other. More specifically, the flask 20 is formed of a left side body 27 and a right side body 28. The left side body 27 and the right side body 28 may be engaged or disengaged using an engaging bolt 35 and a flask engaging nut 36.

Four engaging holes 26 are formed at the corresponding portion of the left side body 27 and the right side body 28. The flask engaging bolt 35 is inserted in the engaging hole 26, and the engaging nut 36 is engaged to the flask engaging bolt 35 inserted in the engaging hole 26, so the left side body 27 and the right side body 28 are engaged with each other.

In addition, the right side body 28 may include a pair of engaging protrusions 31. Engaging grooves (not shown) are formed at the left side body 27 corresponding to the engaging protrusions 31. The engaging protrusions 31 and the engaging grooves are provided in order for the right side body 28 and the left side body 27 to be engaged with each other more reliably.

In addition, a chamfering (not shown) is formed at the lower left sides of the left side body 27 and of the right side body 28. Since the lower corner is chamfered, the left side body may be more easily attached or detached from the right side body.

When the left side body 27 and the right side body 28 are engaged with each other, a chaffered corner and a non-chaffered corner contact with each other, so the engagement and disengagement between the left side body 27 and the right side body 28 may be more easily secured.

Meanwhile, a hollow part 21 is formed in the left side body 27 and the right side body 28, respectively, as illustrated in FIG. 6. A support protrusion 29 is formed in the hollow part 21 of the right side body 28. The hollow part 21 of the right side body 28 is accordingly formed in a shape of a horse hoof.

In addition, when an investment is injected into the inside of the flask 20, the support protrusion 21 serves to reduce the injection amount of the investment. Since the investment is not injected into a portion that does not need the investment thanks to the presence of the support protrusion 21, the investment may be saved.

Namely, an artificial tooth formed of wax is inserted in the horse hoof-shaped hollow part 21 formed at the right side body 28, and the right side body 28 and the left side body 27 are engaged with each other by the flask engaging bolt 35 and the flask engaging nut 36.

Meanwhile, the investment injection port 22, the resin injection port 23 and the guide hole 24 are formed at the upper side of the flask. The investment injection port, the resin injection port 23 and the guide hole 24 are connected to the hollow part 21 of the flask 20.

When gypsum (investment) is injected into the investment insertion port 22, the gypsum is injected into the hollow part 21 of the flask 20. At this time, the worker sees the guide hole 24 formed at the upper side of the flask 20, thus confirming that the gypsum gradually fills in the inside of the flask 20.

In addition, a wax drainage port 25 is formed at the bottom of the flask 20. The wax which has been inputted in the inside of the flask 20 may easily discharge through the wax drainage port 25.

The denture aids inserted in the inside of the flask 20 contains a solid wax. When the flask 20 is heated by a separate heating device, the solid wax is melted and turns into liquid, so the liquid wax flows downward.

Namely, the wax drainage port 25 serves to allow the liquid, which flows downward, to be discharged to the outside of the flask 20. Since the wax drainage port 25 is formed, it does not need to disassemble the flask 20 while the wax is being removed.

In addition, the resin is injected into the resin injection port 23 formed at the upper side of the flask 20 after the wax is discharged to the outside of the flask 20, and the resin is injected through the resin injection port 23 and into the hollow part 21 of the flask 20.

Meanwhile, the flask unit 140 on which the flask 20 is mounted may include a mounting plate 141 on which the flask 20 is mounted, and a cover 144 which serves to open or close the upper side of the flask. The mounting plate 141 and the cover 144 are engaged by means of a pair of support members 147.

As illustrated in FIGS. 1 and 2, a pair of the support members 147 are vertically fixed at one side of the mounting plate 141 on which the flask 20 is mounted. The cover 144 is hinged at an end portion of the support member. In a state where the cover 144 covers the upper side of the flask 20, the vertical cross section of the flask unit 140 is formed in a shape of ⊏.

In addition, the mounting plate 141 on which the flask 20 is mounted may include a pair of flask fixing keys 142 which serve to fix the flask, and a wax collection hole 143 which passes through the upper side and the lower side. The wax collection hole 143 is formed at a portion corresponding to the wax drainage port 25 of the flask, thus allowing the liquid wax flowing through the wax drainage port of the flask 20 to be discharged through the wax collection hole 143 and into the inside of the inner container 120.

In addition, the flask fixing keys 142 are quadrangular protrusions which protrude upward, and are formed on the upper surface of the mounting plate 141 of the portion corresponding to the quadrangular groove formed at the bottom of the flask.

In addition, a pair of engaging bars 148 are vertically fixed at the upper surface of the mounting plate 141, and the engaging bars 148 are formed in a shape of a hollow pipe and include threaded surfaces on their inner circumferential surfaces.

Meanwhile, an engaging hole 149 is formed at the cover 144 at the portion corresponding to the engaging bar 148 of the mounting plate 141, and the engaging hole 149 passes through the upper and lower sides of the cover 144, and a threaded surface is formed at the inner circumferential surface of the engaging hole 149. The user engages the cover 144 and the mounting plate 141 by inserting an engaging bolt 41 through the engaging hole 149 of the cover 144 and the engaging bar 148 of the mounting plate 141.

In addition, a nozzle is installed at the lower side of the cover, namely, at the portion corresponding to the resin injection port 23 of the flask 20 when the flask 20 is mounted on the mounting plate 141. As illustrated in FIG. 3, the nozzle is connected through a water path supply pipe 151 to the water tank 150.

Referring to FIGS. 1 and 3, the water path supply pipe 151 is connected to the water tank 150 and is connected through the inner container 120 and the support plate 130 and to the top of the cover 144. The water path supply pipe 151 is divided into a plurality of pipes in the inside of the cover. The nozzle is connected to each of the pipes.

The plurality of the nozzles serve to supply hot water and steam through the resin injection port 23 of each flask 20 and into the inside of the flask 20.

The water path supply pipe 151 may include a steam supply pipe 155 which is connected to the top of the water tank 150 for supplying steam, and a hot water supply pipe 157 which is connected to the bottom of the water tank 150 for supplying hot water. A control valve is installed where the steam supply pipe 155 and the hot water supply pipe 157 are connected. Steam or hot water may be selectively supplied into the inside of the flask 20 in accordance with an opening and closing of the control valve.

In addition, a packing member 146 is secured to an outer circumferential surface of the nozzle installed at the lower side of the cover 144. The packing member 146 is formed in a ring shape at the portion corresponding to a circular concave groove formed at an outer circumferential surface of the resin injection port 23.

Therefore, when the cover 144 covers the upper side of the flask 20, the packing member of the cover 144 presses the flask 20 from top to bottom, thus fixing the flask 20.

Namely, the flask 20 is mounted on the mounting plate 141, and the left and right sides of the flask are fixed by the flask fixing keys, and the packing member 146 of the cover 144 presses the flask from top to bottom, thus fixing the flask, so that the flask may be more reliably fixed at the flask unit 140.

In addition, a plurality of flasks may be mounted on the mounting plate 141, and in the exemplary embodiment of the present inventive concept, eight flasks, for example, are mounted. The mounting plate 141 may include eight wax collection holes, and eight wax drainage ports, and eight nozzles are installed at the lower side of the cover.

In the present inventive concept, when less than seven flasks are used, a guide rod 170 is inserted into the flask fixing key in which the flask is not inserted and fixed.

The guide rod 170 is formed in a shape of a circular pillar. A protrusion is formed on the upper and lower surfaces. The lower protrusion of the guide rod 170 is fixed by the flask fixing key 142, and the upper protrusion is fixed by the nozzle of the cover 144 and the packing unit, thus blocking the path of the steam and the hot water which flow through the water path supply pipe 151 and into the inside of the flask 20, which makes it possible to enhance work efficiency.

The procedure where the wax inside of the flask is extracted by means of the apparatus for manufacturing a tooth model aids according to the present inventive concept will be described.

First, the worker mounts the flask on the mounting plate 141 of the flask unit 140 and covers the cover 144 and engages the outer housing 110 and the outer cover 111.

In addition, steam is supplied through the steam supply nozzle 122 and into the inside of the inner container. The supply time is set 5~12 minutes. In case where the time for the steam to be supplied into the inside of the inner container 120 is less than 5 minutes, all the solid wax inside of the flask does not melt and flows down, so the wax may not be fully separated from the inside of the flask. In case where the time does not exceed 12 minutes, the solid wax is heated in a state where all the solid wax has been already melted, so such operation is not economical.

Since the steam is supplied into the inside of the inner container 120 and at the same time steam is directly sprayed into the inside of the flask 20, the flask 20 receives the steam through the water path supply pipe 151, and the supply time for the steam to be supplied into the inside of the flask 20 is the same as the time for the steam to be supplied into the inner container 120.

In addition, it needs to wait for 2~5 minutes so that the solid wax can be fully melted by the steam which is sprayed into the inside of the inner container 120. If the waiting time is less than 2 minutes, all the solid wax in the inside of the flak may not melt and flow down, so the wax doesn't fully separate from the inside of the flask 20. If the waiting time is over 5 minutes, it means that all the solid wax has been already melted, so it is non-economical.

Thereafter, hot water is supplied through the water path supply pipe 151 and into the inside of the flask 20, so that the residuals in the inside of the flask may be all melted. If the time for the hot water to be supplied is 3~8 minutes, and the hot water supply time is less than 3 minutes, all the solid wax in the inside of the flask may not be melted and flow down, so the wax does not fully separate from the inside of the flask, and if the time is over 8 minutes, since the solid wax has been already melted, it is non-economical.

Namely, that the hot water is supplied through the water path supply pipe 151 and into the inside of the flask means that the wax which is not melted and resides in the inside of the flask is melted again, so when the hot water is supplied into the inside of the flask, all the solid wax remaining in the inside of the flask may be melted and discharged to the outside of the flask.

In addition, the steam and hot water supplied into the insides of the flask and the inner container 120 and the impurities, for example, wax, etc. melted out of the flask may be discharged through the drainage hole 121 of the inner container 120 and to the outside.

Meanwhile, at the outer cover, a washing gun 162 may be installed so as to wash the inner container 120, etc. A pair of gun holders 161 may be installed at the upper side of the outer cover 111, and the gun 162 may be mounted on the holders 161. One gun may be connected to the top of the water tank 150, thus supplying steam, and the other gun is connected to the bottom of the water tank 150, thus supplying hot water.

Therefore, the present inventive concept has advantages in that the solid wax may be easily removed, which solid wax is used for fixing and dewaxing the tooth model aids so that the denture may be easily and completely dewaxed when molding the tooth model so as to manufacture the dental denture.

As the present inventive concept may be embodied in several forms without departing from the spirit or essential characteristics thereof, it should also be understood that the above-described examples are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

What is claimed is:

1. An apparatus for manufacturing a tooth model, which is configured to dewax when molding a tooth model so as to manufacture a dental denture, comprising:
   an outer housing;
   an outer cover covering the outer housing;
   an inner container installed in an inside of the outer housing; and
   a flask unit installed in an inner space part of the inner container,
   wherein the flask unit includes a mounting plate on which a flask is configured to be mounted, the mounting plate including a wax collection hole on a bottom and having a shape of rectangle, a cover configured to open and close the upper side of the flask, the cover including a nozzle which is configured to selectively inject hot water or steam to the flask, the nozzle being formed at a location corresponding to a location of the flask, a pair of flask fixing keys configured to fix the flask, a wax collection hole, a pair of supporting members vertically fixed at two corners of the rectangle, and a pair of engaging bars vertically fixed at two corners of the rectangle in which the pair of supporting members are not fixed,
   wherein the vertical cross section of the flask unit has a shape of rectangle in which one edge is opened when the cover is closed, and
   wherein the inner container has a vertical cross section formed in a shape of convex isosceles trapezoid shape in which a short base faces a direction away from the outer cover, a bottom surface of the inner container is tilted to form a slanted surface, and a drainage hole is formed at a lower portion of the bottom surface of the inner container.

2. The apparatus of claim 1, further comprising:
   a water tank,
   a steam supply pipe connected between an upper portion of the water tank and the cover, and
   a hot water supply pipe connected between the lower portion of the water tank and the cover.

3. The apparatus of claim 2, further comprising:
   a water path supply pipe selectively connecting the cover to the steam supply pipe or the hot water supply pipe.

4. The apparatus of claim 3, wherein the flask includes a plurality of flasks and the water path supply pipe further comprising branches, each of the branches respectively connected to one of the plurality of flasks.

5. The apparatus of claim 2, wherein the flask includes a plurality of flasks and the water path supply pipe further comprising branches, each of the branches respectively connected to one of the plurality of flasks.

6. The apparatus of claim 2, wherein the inner container includes a drainage hole at a bottom of the inner container, the drainage being formed on the lowest portion of the bottom of the inner container.

7. The apparatus of claim 6, wherein the flask includes a guide hole, a resin injection port, an investment injection hole and a wax drainage port.

8. The apparatus of claim 7, wherein the wax drainage port is formed at the bottom of the flask corresponding to a location of the wax collection hole formed in the mounting plate.

9. The apparatus of claim 1, wherein the inner container includes a drainage hole at a bottom of the inner container, the drainage being formed on the lowest portion of the bottom of the inner container.

10. The apparatus of claim 9, wherein the flask includes a guide hole, a resin injection port, an investment injection hole and a wax drainage port.

11. The apparatus of claim 10, wherein the wax drainage port is formed at the bottom of the flask corresponding to a location of the wax collection hole formed in the mounting plate.

12. The apparatus of claim 1, wherein the flask includes a guide hole, a resin injection port, an investment injection hole and a wax drainage port.

13. The apparatus of claim 12, wherein the wax drainage port is formed at the bottom of the flask corresponding to a location of the wax collection hole formed in the mounting plate.

* * * * *